United States Patent
Pai et al.

(10) Patent No.: US 11,593,665 B2
(45) Date of Patent: Feb. 28, 2023

(54) SYSTEMS AND METHODS DRIVEN BY LINK-SPECIFIC NUMERIC INFORMATION FOR PREDICTING ASSOCIATIONS BASED ON PREDICATE TYPES

(71) Applicant: ACCENTURE GLOBAL SOLUTIONS LIMITED, Dublin (IE)

(72) Inventors: Sumit Pai, Dublin (IE); Luca Costabello, Newbridge (IE)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 355 days.

(21) Appl. No.: 16/892,916

(22) Filed: Jun. 4, 2020

(65) Prior Publication Data

US 2021/0174217 A1    Jun. 10, 2021

Related U.S. Application Data

(60) Provisional application No. 62/954,901, filed on Dec. 30, 2019, provisional application No. 62/944,769, filed on Dec. 6, 2019.

(51) Int. Cl.
  *G06N 5/02*     (2006.01)
  *G06N 20/00*    (2019.01)
  (Continued)

(52) U.S. Cl.
  CPC .............. *G06N 5/02* (2013.01); *G06K 9/6296* (2013.01); *G06N 3/0454* (2013.01); *G06N 3/08* (2013.01); *G06N 20/00* (2019.01)

(58) Field of Classification Search
  CPC .............. G06N 5/02; G06N 3/08; G06N 20/00
  See application file for complete search history.

(56) References Cited

U.S. PATENT DOCUMENTS 10,157,226 B1 * 12/2018 Costabello .......... G06F 16/9024
2018/0144252 A1 * 5/2018 Minervini ............. G06F 9/5005
(Continued)

FOREIGN PATENT DOCUMENTS

AU   2019-200124 A1   8/2019
WO   WO 2019/028179 A1   2/2019

OTHER PUBLICATIONS

Nathani, Deepak, et al. "Learning attention-based embeddings for relation prediction in knowledge graphs." arXiv preprint arXiv: 1906.01195 (Jun. 2019). (Year: 2019).*

(Continued)

*Primary Examiner* — Jialong He
(74) *Attorney, Agent, or Firm* — Crowell & Moring LLP

(57) ABSTRACT

The present disclosure describes methods and systems to predict predicate metadata parameters in knowledge graphs via neural networks. The method includes receiving a knowledge graph based on a knowledge base including a graph-based dataset. The knowledge graph includes a predicate between two nodes and a set of predicate metadata. The method also includes determining a positive structural score, adjusting each positive structural score based on each corresponding significance parameter, generating a synthetic negative graph-based dataset, determining a negative structural score for each synthetic negative triple of the synthetic negative graph-based dataset, adjusting each negative structural score based on each corresponding significance parameter, determining a significance loss value based on the adjusted positive structural scores and the adjusted negative structural scores, and determining a likelihood score of a link between a third node and a fourth node in the knowledge graph based on the significance loss value.

11 Claims, 11 Drawing Sheets

(51) Int. Cl.
*G06K 9/62* (2022.01)
*G06N 3/04* (2023.01)
*G06N 3/08* (2023.01)

(56) References Cited

U.S. PATENT DOCUMENTS

2019/0220524 A1* 7/2019 Costabello ............. G06N 5/045
2020/0074316 A1* 3/2020 Ma ...................... G06F 16/9024

OTHER PUBLICATIONS

Kazemi, Seyed Mehran, and David Poole. "Simple embedding for link prediction in knowledge graphs." Advances in neural information processing systems 31 (2018). (Year: 2018).*

Dettmers, Tim, et al. "Convolutional 2d knowledge graph embeddings." Proceedings of the AAAI Conference on Artificial Intelligence. vol. 32. No. 1. 2018. (Year: 2018).*

Agibetov, Asan, and Matthias Samwald. "Global and local evaluation of link prediction tasks with neural embeddings." arXiv preprint arXiv: 1807.10511 (2018). (Year: 2018).*

Office Action issued on European application 20205888.9 dated Apr. 8, 2021, 9 pages.

Pasquale, Minervini et al., "Leveraging the schema in latent factor models for knowledge graph completion", Proceedings of the 31st Annual ACM Symposium on Applied Computing, SAC '16, ACM Press, New York, NY, Apr. 4, 2016, pp. 327-332.

Krompass, Denis et al., "Type-Constrained Representation Learning in Knowledge Graphs", Advances in Cryptology—Crypto 2018, Part III; Lecture Notes in Computer Science; Springer, Cham. Oct. 30, 2015, pp. 640-655.

First Examination Report in India Application No. 202044048094, dated Jul. 7, 2021, 6 pages.

* cited by examiner

SYSTEMS AND METHODS DRIVEN BY LINK-SPECIFIC NUMERIC INFORMATION FOR PREDICTING ASSOCIATIONS BASED ON PREDICATE TYPES

CROSS-REFERENCE TO RELATED APPLICATION

This application claims benefit to U.S. Provisional Patent Application No. 62/944,769 filed on Dec. 6, 2019 and U.S. Provisional Patent Application No. 62/954,901 filed on Dec. 30, 2019, the entireties of which are incorporated by reference herein.

FIELD OF THE INVENTION

The present disclosure relates in general to the field of knowledge graphs, and in particular methods and systems that utilize neural networks to predict predicate metadata parameters for graph-base datasets used to generate knowledge graphs.

BACKGROUND

Basic techniques and equipment for machine learning, modeling data, and graph embedding are known in the art. While enterprise systems have access to large volumes of information relating to human genetic makeup, genetic mutation information, gene expression information, drug interactions, molecular structures, and disease classification. Existing analytical applications and data warehousing systems have not been able to fully utilize such information. Often times, information is simply aggregated into large data warehouses without proper data quality screening and the inclusion of an added layer of relationship data connecting the information. Such aggregation of large amounts of data, without contextual or relational information, are data dumps that are not useful.

Information stored in their original format in data warehouses often requires large amounts of computing resources to transform the information into searchable data in order to respond to a query using string matching mechanisms (semantic linking) without context. Such conventional approaches are limited in their ability to identify and return queried data, and most of the stored data is not easily configured for machine learning analytics to provide a complete picture of knowledge and data in the enterprise. A multi-relational link prediction is desired to more efficiently and effectively identify predicates for gene-disease associations.

SUMMARY

The present disclosure describes a system for predicting node-to-node links in a knowledge graph. The system includes a memory to store executable instructions and a processor adapted to access the memory. The processor is further adapted to execute the executable instructions stored in the memory to receive a knowledge graph based on a knowledge base, the knowledge graph comprising a link between a first node and a second node, the first and second nodes representing associated objects, the knowledge base comprising a graph-based dataset stored in the memory, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph. The processor is further adapted to execute the executable instructions stored in the memory to determine a positive structural score for each triple in the knowledge graph, adjust each positive structural score based on each corresponding significance parameter, generate a synthetic negative graph-based dataset based on the graph-based dataset, the synthetic negative graph-based dataset comprising a set of synthetic negative triples, and determine a negative structural score for each synthetic negative triple of the synthetic negative graph-based dataset. The processor is further adapted to execute the executable instructions stored in the memory to adjust each negative structural score based on each corresponding significance parameter, determine a significance loss value based on the adjusted positive structural scores and the adjusted negative structural scores, and determine a likelihood score of a link between a third node and a fourth node in the knowledge graph based on the significance loss value.

The present disclosure describes a method for predicting node-to-node links in a knowledge graph. The method includes receiving, by a device, a knowledge graph based on a knowledge base. The device includes a memory storing instructions and a processor in communication with the memory. The knowledge graph includes a link between a first node and a second node, the first and second nodes representing associated objects, the knowledge base includes a graph-based dataset stored in the memory, the graph-based dataset associating the first node with the second node, the graph-based dataset of the knowledge base includes a set of predicate metadata assigned to each triple in the knowledge graph, the graph-based dataset of the knowledge base includes a significance parameter assigned to each triple in the knowledge graph. The method also includes determining, by the device, a positive structural score for each triple in the knowledge graph, adjusting, by the device, each positive structural score based on each corresponding significance parameter, generating, by the device, a synthetic negative graph-based dataset based on the graph-based dataset, the synthetic negative graph-based dataset comprising a set of synthetic negative triples, determining, by the device, a negative structural score for each synthetic negative triple of the synthetic negative graph-based dataset, and adjusting, by the device, each negative structural score based on each corresponding significance parameter. The method also includes determining, by the device, a significance loss value based on the adjusted positive structural scores and the adjusted negative structural scores, and determining, by the device, a likelihood score of a link between a third node and a fourth node in the knowledge graph based on the significance loss value.

The present disclosure describes a product including machine-readable media other than a transitory signal and instructions stored on the machine-readable media for optimizing hyper-parameters for a machine-learning model under constraints. When a processor executes the instructions, the product is configured to receive a knowledge graph based on a knowledge base, the knowledge graph comprising a link between a first node and a second node, the first and second nodes representing associated objects, the knowledge base comprising a graph-based dataset stored in the memory, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph. When a processor executes the instructions, the product is configured to determine a positive structural score for each triple in the knowledge graph, adjust each positive structural score based on each corresponding significance parameter, generate a synthetic negative graph-based dataset based on the graph-based dataset, and the synthetic negative graph-based dataset comprising a set of synthetic negative triples. When a processor executes the instructions, the product is configured to determine a negative structural score for each synthetic negative triple of the synthetic negative graph-based dataset, adjust each negative structural score based on each corresponding significance parameter, determine a significance loss value based on the adjusted positive structural scores and the adjusted negative structural scores, and determine a likelihood score of a link between a third node and a fourth node in the knowledge graph based on the significance loss value.

BRIEF DESCRIPTION OF THE DRAWINGS

The foregoing and other objects, features, and advantages for embodiments of the present disclosure will be apparent from the following more particular description of the embodiments as illustrated in the accompanying drawings, in which reference characters refer to the same parts throughout the various views. The drawings are not necessarily to scale, emphasis instead being placed upon illustrating principles of the present disclosure.

DETAILED DESCRIPTION

Figure 1:
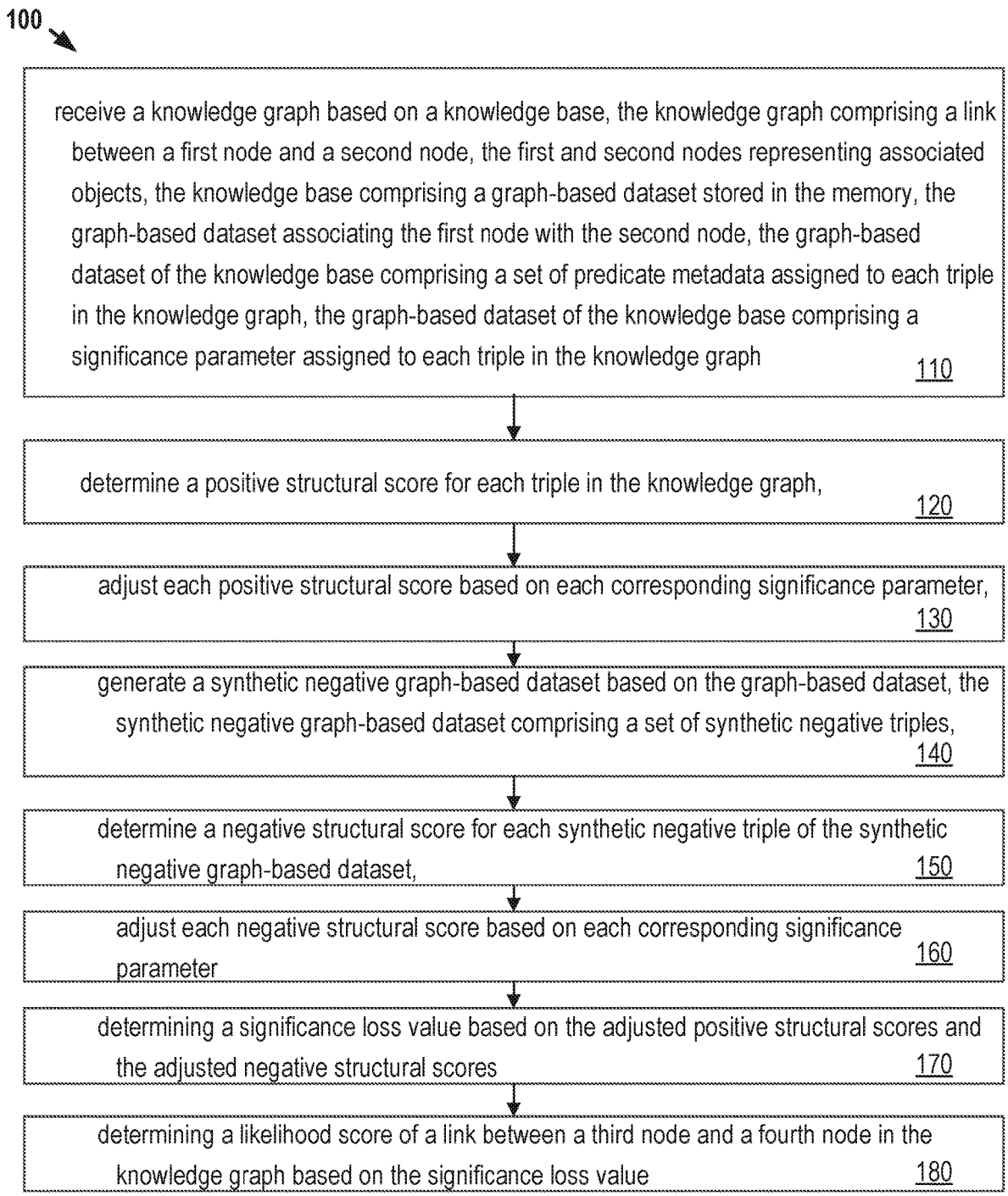
FIG. 1 is a flow diagram illustrating an example of a method implemented by an exemplary system, in accordance with certain embodiments of the present disclosure.

Reference will now be made in detail to the embodiments of the present disclosure, examples of which are illustrated in the accompanying drawings, which form a part of the present disclosure, and which show, by way of illustration, specific examples of embodiments. Please note that the disclosure may, however, be embodied in a variety of different forms and therefore, the covered or claimed subject matter is intended to be construed as not being limited to any of the embodiments to be set forth below. Please also note that the disclosure may be embodied as methods, devices, components, or systems. Accordingly, embodiments of the disclosure may, for example, take the form of hardware, software, application program interface (API), firmware or any combination thereof.

Throughout the specification and claims, terms may have nuanced meanings suggested or implied in context beyond an explicitly stated meaning. Likewise, the phrase "in one embodiment" or "in one implementation" as used herein does not necessarily refer to the same embodiment or implementation and the phrase "in another embodiment" or "in another implementation" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context.

In addition, the term "based on" or "determined by" may be understood as not necessarily intended to convey an exclusive set of factors and may, instead, allow for existence of additional factors not necessarily expressly described, again, depending at least in part on context.

The present disclosure may be embodied in various forms, including a system, a method, a computer readable medium, or a platform-as-a-service (PaaS) product for identifying predicate-types for graph-based datasets used to generate knowledge graphs and predicting missing links with high accuracy using neural networks or machine-learning models selected based on the targeted predicate-types. In an example, the present disclosure may be applied to amend a positive structural score for a link based on a significance parameter, and to also amend a negative structural score for the link based on the significance parameter.

In an embodiment, this disclosure may provide a framework for a system adapted to receive a pre-existing knowledge graph, and/or a knowledge base corresponding the pre-existing knowledge graph. The knowledge base, and its knowledge graph, may relate to information concerning various fields, such as an airline, a finance, a telecommunication, a restaurant, or a medical industry. In an embodiment, the knowledge graph may represent datasets concerning associations or links between a gene and a disease. The knowledge graph may also include a significance, or importance, parameter assigned to each graph-based dataset of the knowledge base.

In some embodiments, the system may determine a positive structural score for each graph-based dataset of the knowledge base. The system may amend the positive structural score based on the significance parameter. In addition, the system may generate a synthetic negative graph-based dataset. The neural networks, or machine-learning models, may be trained on both true and false statements/facts. In an embodiment, the synthetic negative graph-based dataset may be generate based a reversal or inversion of a predicate or association for a random portion of the graph-based datasets. The system may determine a negative structural score for each graph-based dataset of the set of synthetic negative graph-based dataset. The system may also amend the negative structural score based on the significance parameter.

In certain embodiments, the system may determine a significance loss value based on the amended positive structural score and the amended negative structural score. The system may include a plurality of neural networks configured to predict or generate a set of predicate metadata parameters. The system may determine a predicate metadata loss value for the set of predicate metadata parameters. The system may also determine an overall loss value based on the significance loss value and the predicate metadata loss value.

The system may minimize the overall loss value using a machine learning model, in accordance with some embodiments. The system may determine a trained model based on the minimized overall loss value. In addition, the system may receive a real-time user input request of a graph-based dataset. The system may determine a likelihood score of a link between a gene and a disease based on the trained model and the user input request.

The present disclosure may be embodied in a system, method and computer readable medium for predicting node-to-node links in a knowledge graph. A knowledge base of gene-related and disease-related data, and their associated relationships or links, may be represented in a meaningful and understandable manner via a knowledge graph, in accordance with certain embodiments. A model for a knowledge graph may be defined by a schema or layout that describes the data structures and their relationships, which may be represented by nodes and edges in the knowledge graph. The knowledge graph may present complex and innovative graphical structures that represent the relevant information in response to a query. In an embodiment, the knowledge graph may represent the knowledge base via graphical representations that correspond to structured data points or entities (represented by nodes), relationships (represented by edges), and attributes (represented by node properties or edge properties) with semantic meaning.

The present disclosure describes one embodiment for a method driven by link-specific numeric information for predicting associations based on predicate types. Referring to FIG. 1, a method 100 may include a portion or all of the following: step 110: receive a knowledge graph based on a knowledge base, the knowledge graph comprising a link between a first node and a second node, the first and second nodes representing associated objects, the knowledge base comprising a graph-based dataset stored in the memory, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph; step 120: determine a positive structural score for each triple in the knowledge graph; step 130: adjust each positive structural score based on each corresponding significance parameter, step 140: generate a synthetic negative graph-based dataset based on the graph-based dataset, the synthetic negative graph-based dataset comprising a set of synthetic negative triples, step 150: determine a negative structural score for each synthetic negative triple of the synthetic negative graph-based dataset, step 160: adjust each negative structural score based on each corresponding significance parameter, step 170: determine a significance loss value based on the adjusted positive structural scores and the adjusted negative structural scores, and step 180: determine a likelihood score of a link between a third node and a fourth node in the knowledge graph based on the significance loss value.

Figure 2:
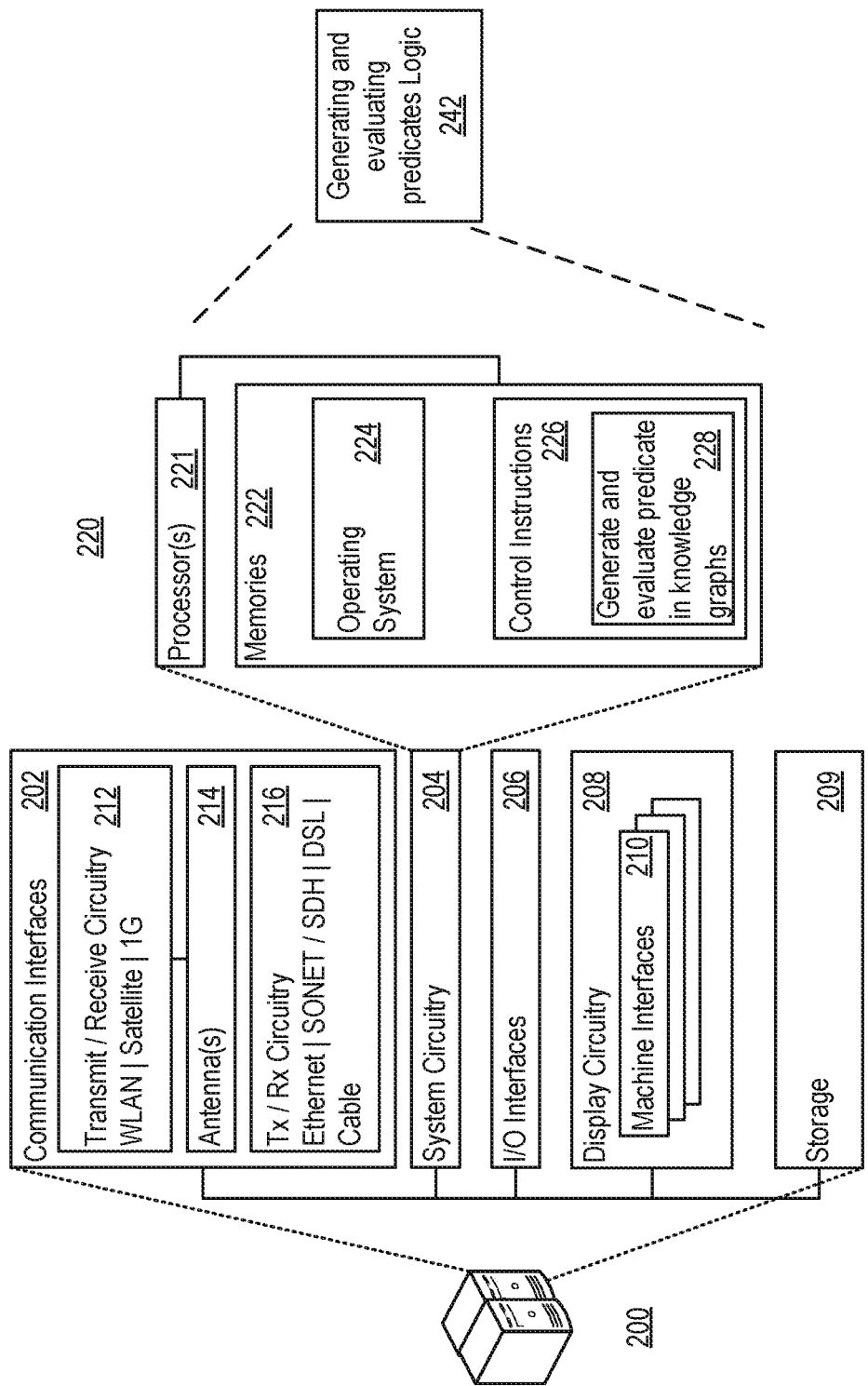
FIG. 2 is a block diagram illustrating an embodiment of a computer architecture for a device for implementing the method in FIG. 1, in accordance with certain embodiments of the present disclosure.

FIG. 2 shows an example execution circuitry 200 for implementing the method 100. The execution circuitry 200 may include a computer system 200 for implementing the method 100.

Referring to FIG. 2, the execution circuitry 200 may include communication interfaces 202, system circuitry 204, input/output (I/O) interfaces 206, storage 209, and display circuitry 208 that generates machine interfaces 210 locally or for remote display, e.g., in a web browser running on a local or remote machine. The machine interfaces 210 and the I/O interfaces 206 may include GUIs, touch sensitive displays, voice or facial recognition inputs, buttons, switches, speakers and other user interface elements. Additional examples of the I/O interfaces 206 include microphones, video and still image cameras, headset and microphone input/output jacks, Universal Serial Bus (USB) connectors, memory card slots, and other types of inputs. The I/O interfaces 206 may further include magnetic or optical media interfaces (e.g., a CD ROM or DVD drive), serial and parallel bus interfaces, and keyboard and mouse interfaces. The display circuitry 208 may include man-machine interfaces and/or graphical user interfaces (GUI). The GUI may be used to present interfaces and/or options to facilitate model management and/or the execution of other tasks.

The communication interfaces 202 may include wireless transmitters and receivers ("transceivers") 212 and any antennas 214 used by the transmitting and receiving circuitry of the transceivers 212. The transceivers 212 and antennas 214 may support Wi-Fi network communications, for instance, under any version of IEEE 802.11, e.g., 802.11n or 802.11ac. The communication interfaces 202 may also include wireline transceivers 216. The wireline transceivers 116 may provide physical layer interfaces for any of a wide range of communication protocols, such as any type of Ethernet, data over cable service interface specification (DOCSIS), digital subscriber line (DSL), Synchronous Optical Network (SONET), or other protocol. Additionally or alternatively, the communication interface 202 may support secure information exchanges, such as secure socket layer (SSL) or public-key encryption-based protocols for sending and receiving private data.

The storage 209 may be used to store various initial, intermediate, or final data or model for implementing the method 100 in FIG. 1. These data corpus may alternatively be stored in a database. In one implementation, the storage 209 of the computer system 200 may be integral with the database. The storage 209 may be centralized or distributed, and may be local or remote to the computer system 200. For example, the storage 209 may be hosted remotely by a cloud computing service provider.

The system circuitry 204 may include hardware, software, firmware, or other circuitry in any combination. The system circuitry 204 may be implemented, for example, with one or more systems on a chip (SoC), application specific integrated circuits (ASIC), microprocessors, discrete analog and digital circuits, and other circuitry.

The system circuitry 204 may support tasks described in the present disclosure, including the drawings and/or claims. In one example, the system circuitry 204 may be implemented as processing circuitry 220 for implementing generating and evaluating predicates logic 242, which may provide software support to implement the various tasks performed in the method 100 of FIG. 1. The processing circuitry 220 may include one or more processors 221 and one or more memories 222. The memories 222 stores, for example, control instructions 226 and an operating system 224. The control instructions 226, for example may include instructions for implementing the task of predicting node-to-node links in knowledge graphs 228. In one implementation, the one or more processors 221 execute the control instructions 226 and the operating system 224 to carry out any desired functionality described in the present disclosure.

Referring to FIG. 2, the memories 222 may further include applications and structures, for example, coded objects, templates, or one or more other data structures to facilitate model management and/or the execution of other tasks.

Referring to step 110 in FIG. 1, the method 100 may include receiving, by a device, a knowledge graph based on a knowledge base. The device may be an execution circuitry 200 in FIG. 2, including a memory storing instructions and a processor in communication with the memory. The knowledge graph includes a predicate between a first node and a second node, and the first and second nodes represent associated objects. The knowledge base includes a graph-based dataset stored in a memory in communication with the processor, and the graph-based dataset includes an association of the first node with the second node.

Figure 3A:
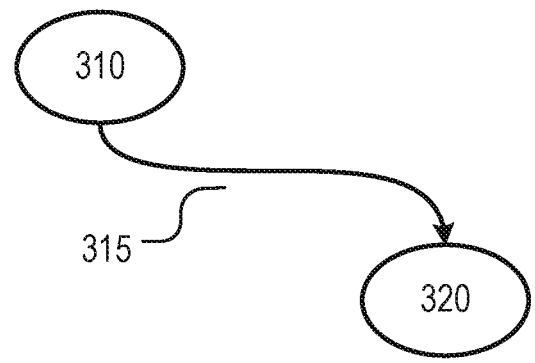
FIG. 3A is a schematic diagram illustrating a knowledge graph schema, in accordance with certain embodiments of the present disclosure.
Figure 3B:
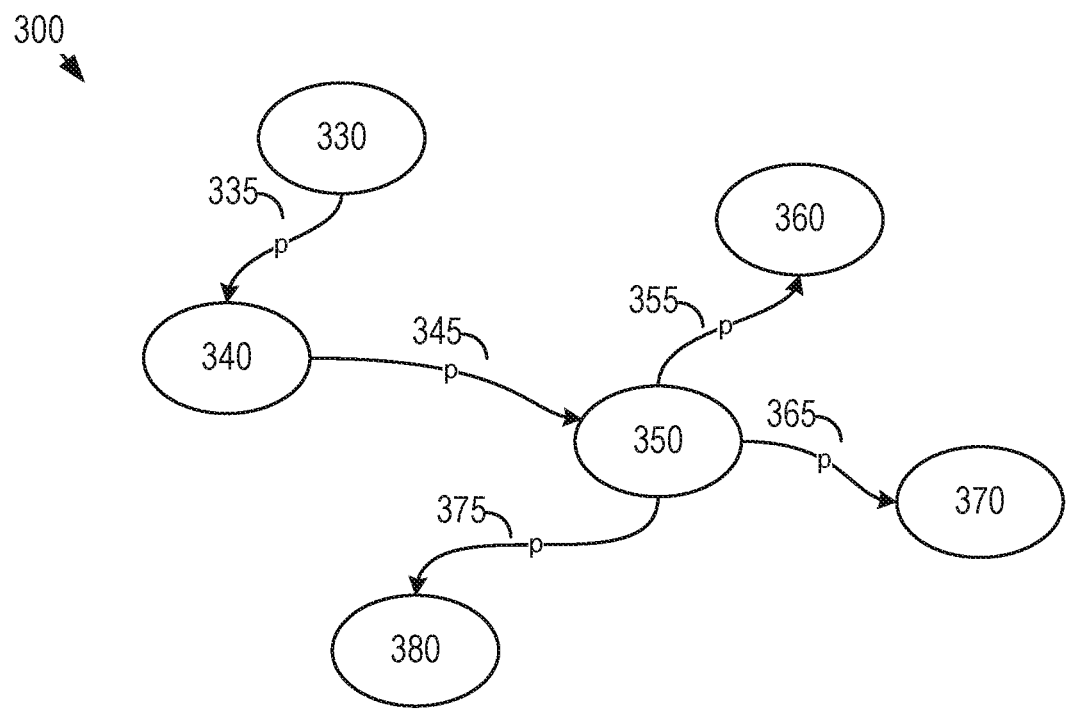
FIG. 3B is a schematic diagram illustrating a knowledge graph schema, in accordance with certain embodiments of the present disclosure.

Referring to FIG. 3A, an example of a knowledge graph may include a first node 310, a second node 320, and a link 315 between the first node 310 and the second node 320. The link 315 may be a predicate. The first and second nodes (310 and 320) may represent associated objects, respectively. The link or predicate may have a directionality pointing from the first object associated with the first node 310 to the second object associated with the second node 320. Referring to FIG. 3B, another example of a knowledge graph 300 may include a plurality of nodes (330, 340, 350, 360, 370, and 380) and a plurality of links or predicates (335, 345, 355, 365, and 375) between the plurality of nodes.

The knowledge base may include one or more graph-based datasets. The graph-based datasets may be stored in the memory and includes associations of the corresponding two nodes, for example, a graph-based dataset may include an association of the first node and the second node. In one implementation, a graph-based dataset may include data records having three parameters, which may be known as a triple: a subject, an object, and a predicate that represents a relationship between the subject and the object. For example, a predicate "causes" may represent an association between a subject representing a "gene" and an object representing a "disease." Optionally in some implementations, a graph-based dataset may include data records having an additional fourth parameter, such as a significance/importance parameter. This fourth parameter may be considered an attribute of the predicate parameter. In some implementations, the fourth parameter may comprise metadata.

Referring to FIG. 3A, a knowledge graph may visually represent a graph-based dataset by displaying two nodes (310 and 320) connected by a link 315 with a unidirectional arrow, which represent a predicate in a triple. The two nodes may represent associated objects, such as physical objects or concepts.

Referring to step 110 in FIG. 1, the graph-based dataset of the knowledge base may include a set of predicate metadata assigned to each triple in the knowledge graph. The number of predicate metadata parameters in each set may depend on the type of the predicate. The significance parameter may be shown as a value assigned to the unidirectional arrows.

In one implementation, the method 100 may include generating, by the device, a set of predicate metadata parameters based on a plurality of neural networks. The generated set of predicate metadata parameters may include the set of predicate metadata parameters assigned to each graph-based dataset of the knowledge base.

Referring to step 110 in FIG. 1, the graph-based dataset of the knowledge base may include a significance parameter assigned to each triple in the knowledge graph.

In one embodiment, the graphically represented data offered by the knowledge graph may provide semantic meaning for the knowledge base by modeling the data via ontology, such as a schema. The knowledge graph may represent graph-based datasets that describe the relationship or predicate between a subject (e.g., a gene) and an object (e.g., a disease).

Figure 4:
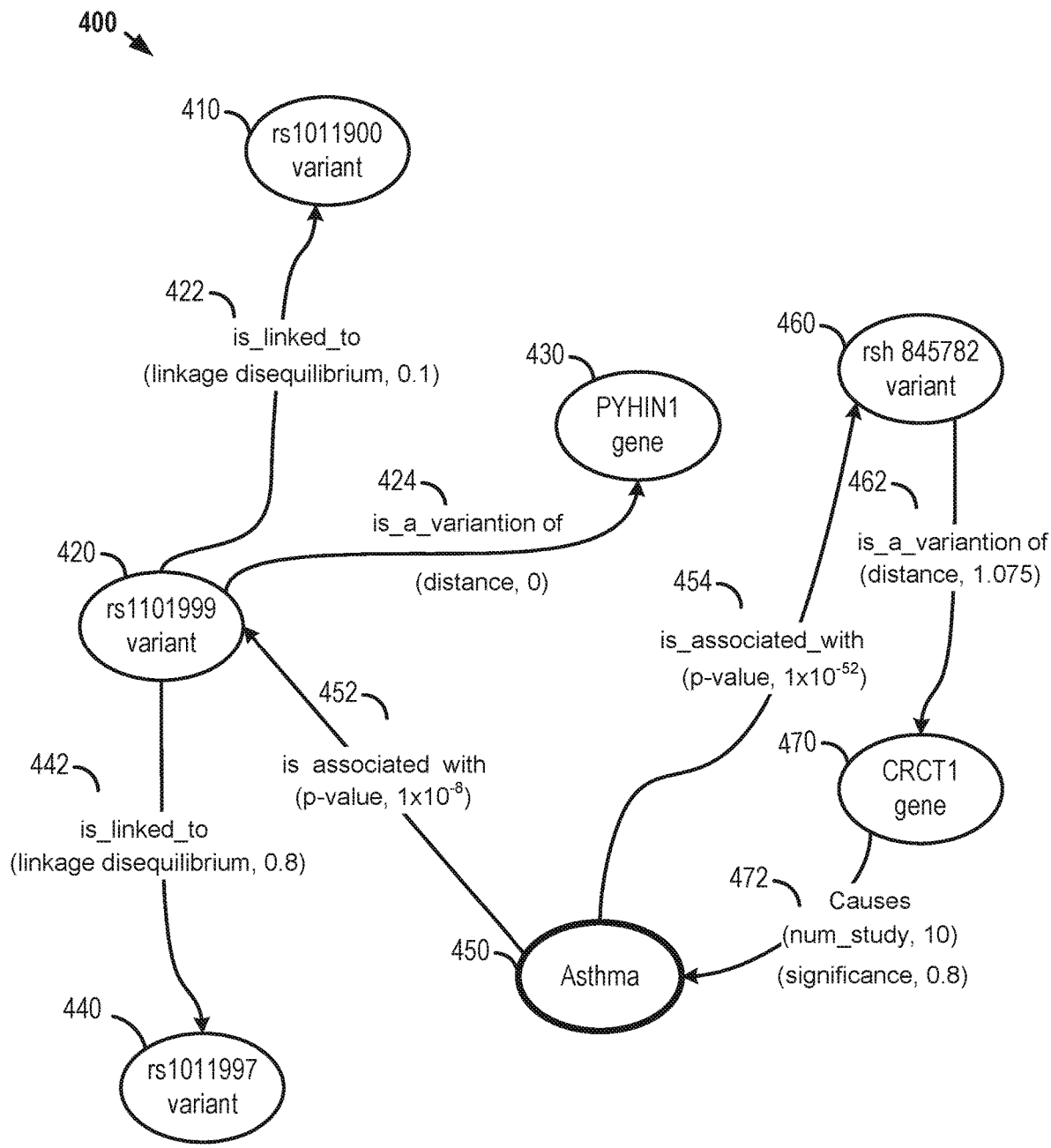
FIG. 4 is a schematic diagram illustrating a knowledge graph schema, in accordance with certain embodiments of the present disclosure.

Referring to FIG. 4, in one implementation, a knowledge graph schema 400 is described as an example within the scope of genes, diseases and associated information, in accordance with certain embodiments of the present disclosure. The schema may describe specific concepts or categories in various formats and data structures, e.g. classes in object-oriented data models or programming languages. The schema may provide a manner to express statements about the resources or knowledge base using specific properties that describe the knowledge base. For example, a Resource Description Framework (RDF) may provide a data model that represents the knowledge base in expressions of the form subject-predicate-object. In one implementation, the knowledge base may be expressed by graph-based datasets or triples, which includes one subject, one object, and a link or predicate. The link or predicate may include one or more numerical attributes.

Referring to the knowledge graph 400 in FIG. 4, a node 410 may represent rs1011900 variant; a node 420 may represent rs1101999 variant; a node 430 may represent PYHIN1 gene; a node 440 may represent rs1011997 variant; a node 450 may represent asthma; a node 460 may represent rsh845782 variant; and a node 470 may represent CRCT1 gene.

The subject may denote the resource, and the predicate may denote traits or aspects of the resource and express a relationship between the subject and the object. In an example, the statement "the gene causes the disease" in the RDF model may be represented as a triple: a subject denoting the "Gene"; a predicate denoting "Causes"; and an object denoting "Disease." Another example of a statement in such a RDF model may include "the disease is associated with a gene," where the triple may comprise a "Disease" subject, an "is associated with" predicate, and a "Gene" object. In the example in FIG. 4, the node 450 "astham" represents a disease; and the node 470 "CRCT1 gene" represents a gene.

Referring to FIG. 4, a link or predicate 422 from the node 420 to the node 410 may include "is_linked_to." The link or predicate 422 may include numerical attributes as "linkage disequilibrium, 0.1." Optionally in one implementation, "is_linked_to" may be taken as a predicate type.

A link or predicate 424 from the node 420 to the node 430 may include "is_a_variation of." The link or predicate 424 may include numerical attributes as "distance, 0." Optionally in one implementation, "is_a_variation of" may be taken as another predicate type.

A link or predicate 442 from the node 440 to the node 420 may include "is_linked_to." The link or predicate 442 may include numerical attributes as "linkage_disequilibrium, 0.8."

A link or predicate 452 from the node 450 to the node 420 may include "is_associated with." The link or predicate 452 may include numerical attributes as "p-value, 1×10-8." Optionally in one implementation, "is_associated with" may be taken as another predicate type.

A link or predicate 454 from the node 450 to the node 460 may include "is_associated with." The link or predicate 454 may include numerical attributes as "p-value, 1×10-52."

A link or predicate 462 from the node 460 to the node 470 may include "is_a_variation of." The link or predicate 462 may include numerical attributes as "distance, 1.075."

A link or predicate 472 from the node 470 to the node 450 may include "causes." The link or predicate 472 may include numerical attributes as "num_study, 10" and "significance, 0.8." Optionally in one implementation, "causes" may be taken as another predicate type.

In one embodiment, the link (also, predicates or edges) between the nodes in the knowledge graph may be weighted. In one implementation, the knowledge graph may comprise a labelled, directed multi-graph representing a dataset with multiple numerical attributes associated to each link, which may be denoted by the variable t and defined as $t=(s,\rho,o,w,[\delta_1, \ldots \delta_n])$, where s is the subject of the resource or knowledge base, o is the object, $\rho$ is the predicate that denotes traits or aspects of the resource that express the relationship or link between the subject and the object in a graph-based dataset format, w is the significance parameter, and $\vec{\delta}=[\delta_1, \ldots \delta_n]$ are informational-type numerical attributes.

Taking the link or predicate 472 in FIG. 4 as one example, the predicate 472 may be represented by a variable t, which may include s being CRCT1 gene, o being asthma, $\rho$ being "causes", w being the significance parameter of 0.8, and S including "num_study" of 10.

In some embodiments, a numerical attribute may be categorized into two types: a significance-type numerical attribute; and an informational-type numerical attribute. For example, in accordance with certain significance-type numerical attributes, the significance parameter w may represent the importance of the link or relationship between the subject and the object. This may be assigned by human annotators, or by computing the inverse frequency of links, from out-of-band external experiments, and/or uncertainty estimates. In accordance with certain informational-type numerical attributes, the numerical attributes $[\delta_1, \ldots \delta_n]$ may represent additional information concerning the link, such as the distance of a variant to the gene. The size of $\vec{\delta}$ may be dependent on the predicate.

Figure 5:
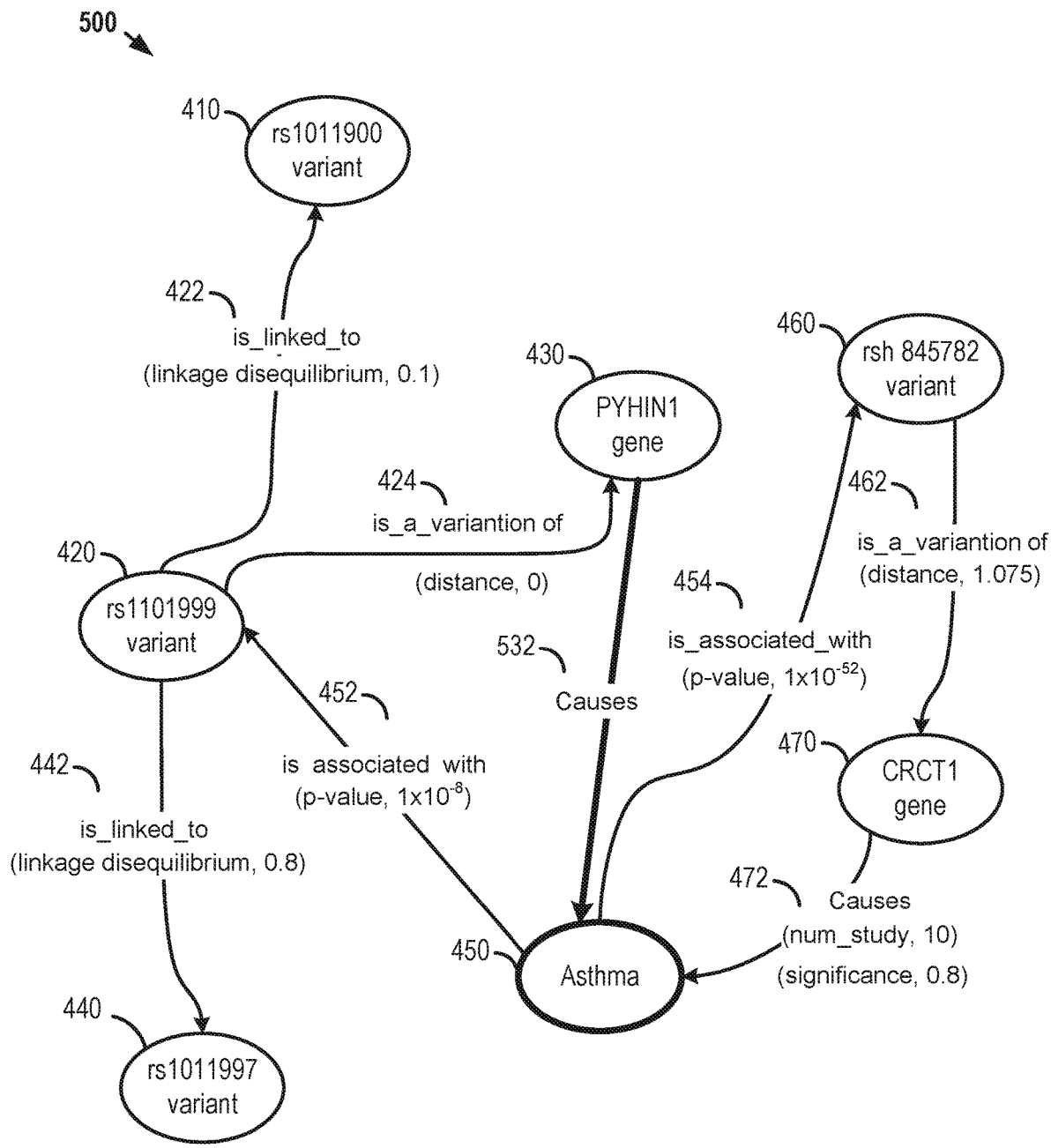
FIG. 5 is a schematic diagram illustrating a missing link predicted in the knowledge graph shown in FIG. 4, in accordance with certain embodiments of the present disclosure.

Referring to FIG. 5, in one implementation, the method 100 may include predicting associations between nodes in a knowledge graph 500. The discovery of information represented in a knowledge base may be appreciated by knowledge graphs that model complex interactions between concepts. Machine learning may be utilized to predict missing links between nodes, i.e. concepts. Basic techniques and frameworks for relational learning may include: knowledge graph embeddings (KGE), such as the TransE model, RESCAL, DistMult, ComplEx, and ConvE; graph neural networks (GNN), such as Graph Convolution Network (GCN), weighted graph convolution network (WGCN), and GraphSAGE; and node representation learning.

For example, there is no link between the node 430 and the node 450 in the knowledge graph 400 in FIG. 4. As shown in FIG. 5, a previously-missing link 532 from the node 430 and the node 450 may be predicted. The link 532 may include "causes".

Figure 6:
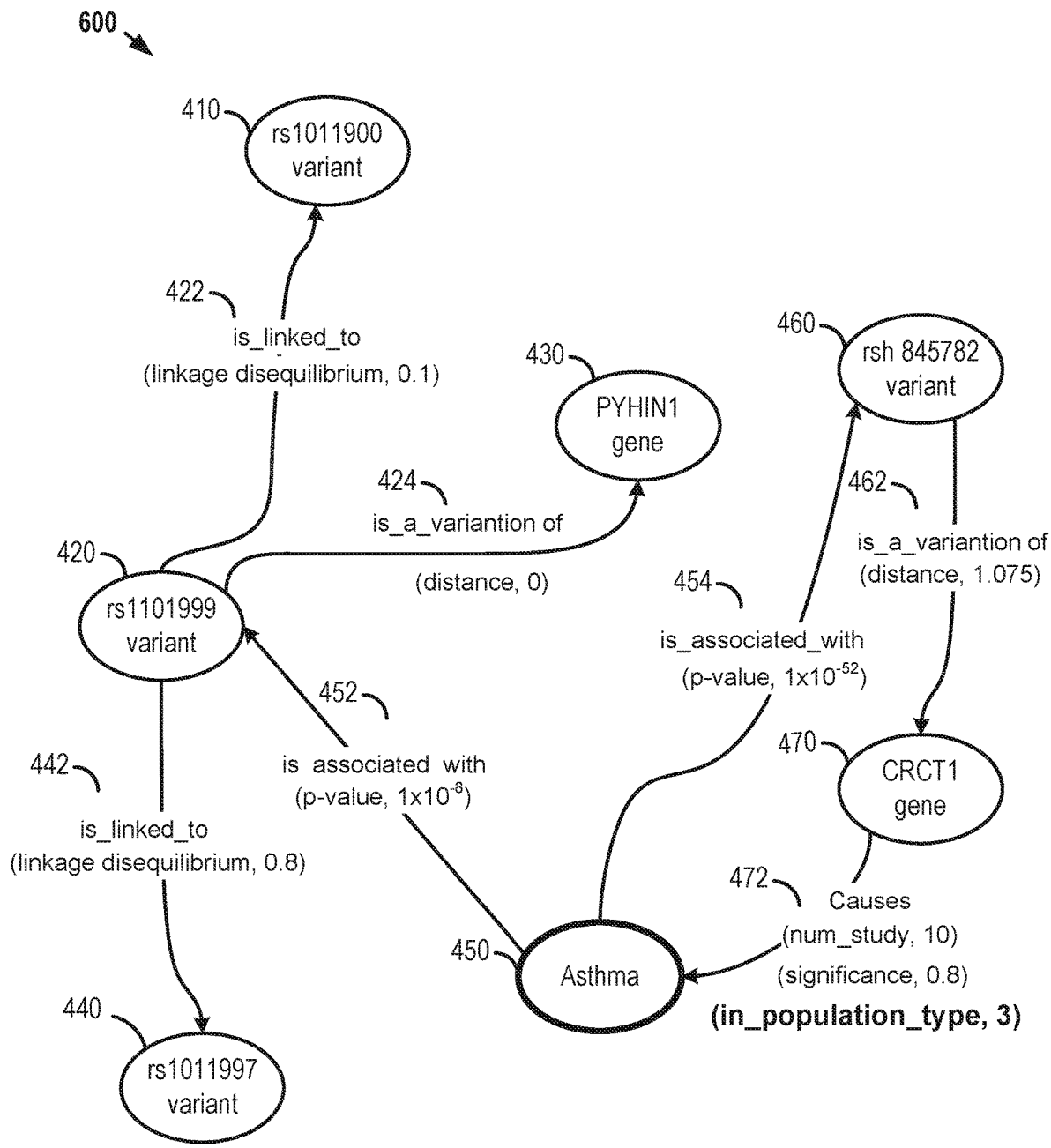
FIG. 6 is a schematic diagram illustrating a knowledge graph showing associations between a disease and certain genes and variants, including specific types of numerical attributes for their associations, in accordance with certain embodiments of the present disclosure.

Referring to FIG. 6, in another implementation, the method 100 may include assigning one or more predicate metadata parameters to a link or predicate in a knowledge graph 600. The knowledge graph 400 in FIG. 4 may represent a collection of RDF statements linking the Asthma disease to the CRCT1 and PYHIN1 genes, and the variants of the genes. The RDF statements may be represented by the knowledge graph with labeled vertices or nodes, and labeled edges that may have a distinguished direction. Such knowledge graphs may be complex multigraphs that include multiple adjacencies or edges, including self-loops, between multiple vertices or nodes. For example, a disease may be associated with a gene or its variant. A data structure for the corresponding knowledge base may have properties, which may be represented as subjects or objects of graph-based dataset, as defined by the knowledge graph schema.

For example, as shown in FIG. 6, a gene-disease association may include an "in_population_type" informational-type numerical attribute as a predicate metadata parameter for the link or predicate 472, and the method 100 may assign a value of 3 to the "in_population_type" informational-type numerical attribute.

In one implementation, the method 100 may include amending a positive structural score for a link based on a significance parameter, and also amending a negative structural score for the link based on the significance parameter. In another implementation, the method 100 may include determining a positive structural score for each graph-based dataset of the knowledge base. The method 100 may also include amending the positive structural score based on the significance parameter. In addition, the method 100 may include generating a set of synthetic negative graph-based datasets. The neural networks, or machine-learning models, may be trained on both true and false statements/facts.

In another implementation, the method 100 may include generating synthetic negative graph-based datasets based a reversal or inversion of a predicate or association for a random portion of the graph-based datasets. The method 100 may include determining a negative structural score for each graph-based dataset of the set of synthetic negative graph-based dataset. The method 100 may also include amending the negative structural score based on the significance parameter. In one implementation, the method 100 may include determining a significance loss value based on the amended positive structural score and the amended negative structural score. The method 100 may include using a plurality of neural networks configured to predict or generate a set of predicate metadata parameters. The method 100 may include determining a predicate metadata loss value for the set of predicate metadata parameters. The method 100 may include determining an overall loss value based on the significance loss value and the predicate metadata loss value.

Referring to step 170 in FIG. 1, the method 100 may include determining a significance loss value based on the adjusted positive structural scores and the adjusted negative structural scores. Optionally, the method 100 may include step 180: determining a likelihood score of a link between a third node and a fourth node in the knowledge graph based on the significance loss value.

In an embodiment, the technical improvements realized by the present disclosure may include predicting, with high accuracy, missing links of a specific type in a knowledge graph with numerical values associated to the known links. In certain embodiments, the system and method may be focused on predicting only specific predicate types. A drawback of some existing technics includes their broad spectrum, i.e. they are designed to complete a graph. In other words, they attempt to predict links regardless of the predicate type. In accordance with certain embodiments, a multi-relational link prediction is desired to focus on a specific link type. A benefit of the present disclosure may include more accurate link predictions in a shorter amount of time. Calculations may be performed to predict the relationship between a gene and a disease, and rank the predictions using scoring functions. In certain embodiments, the gene for a disease may be identified based on human biological data and gene variation data. In an example, the present disclosure may provide a framework for new analytics to identify the probability of existence of links between a gene and a disease.

In some embodiments, this disclosure may assist a discovery scientist to answer key scientific questions about gene-disease associations before going into clinical trial. Such information will result in the improved treatment of patients. The present disclosure may provide a novel framework for predicting specific predicate types. In some embodiments, the system may include a defined schema for connecting different data sources that may be employed in various analytics methods. This may include the use of weighted edges in a knowledge graph for discovering new links. These weights may influence the prediction scores of identified links.

In some embodiments, the step 180 in FIG. 1 may include a portion or all of the following: determining a predicate metadata loss value for the assigned set of predicate metadata parameters; and determining the likelihood score of the link between the third node and the fourth node in the knowledge graph based on the significance loss value and the predicate metadata loss value, which may include determining an overall loss value based on the significance loss value and the predicate metadata loss value; minimizing the overall loss value based on a machine learning model; and determining the likelihood score of the link between the third node and the fourth node in the knowledge graph based on the minimized overall loss value.

In some embodiment, the determining the likelihood score of the link between the third node and the fourth node in the knowledge graph based on the minimized overall loss value may include determining a trained model based on the minimized overall loss value; receiving a real-time user input request of a graph-based dataset; determining the likelihood score of the link between the third node and the fourth node based on the trained model and the user input request; and updating the knowledge graph with the link.

In some embodiment, the numerical attributes for a knowledge graph may include one or more of the following attributes: the importance categorization of attributes, which may include a significance parameter w assigned to a graph-based dataset; and the information categorization of attributes, which may include a numerical attribute for the distance of a gene to its variant.

Figure 7:
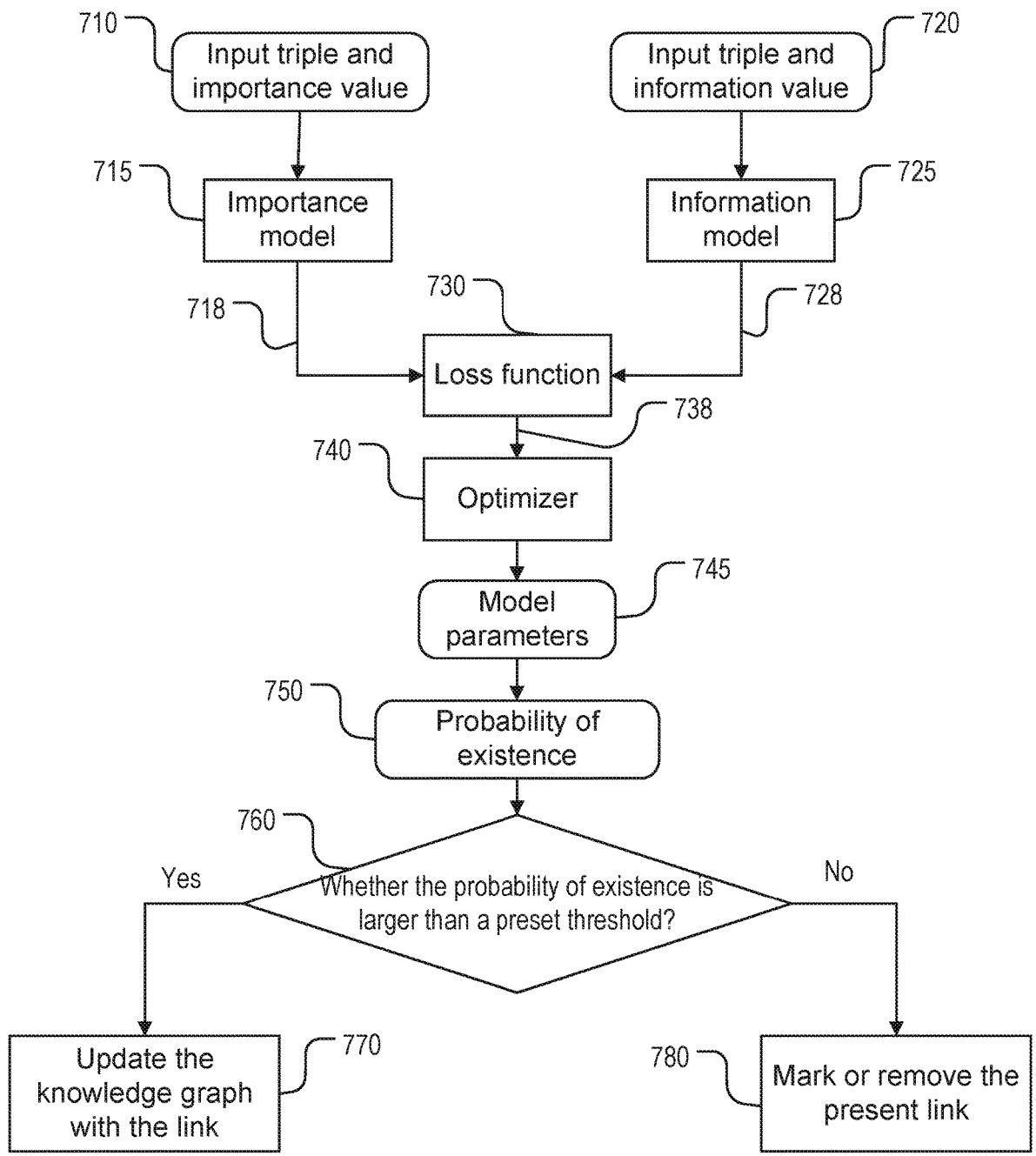
FIG. 7 is a block diagram illustrating an exemplary implementation of numerical input received from a knowledge graph in an importance model, an information model, a loss function calculation, machine learning models, a scoring determination, and link prediction for an association between nodes, in accordance with certain embodiments of the present disclosure.

Referring to FIG. 7, the input triple and importance value 710 may be utilized as importance input to an importance model 715; and the input triple and information value 720 may be utilized as information input to an information model 725. In one implementation, for the knowledge graph 600 in FIG. 6, the importance inputs may include a portion or all of the following: <CRCT1, causes, Asthma, 0.8>, and <Asthma, is_associated_with, rsh845782 variant, 1×10-52>. In another implementation, the information inputs may include a portion or all of the following: <rs1101999, is_a_variation_of, PYHIN1, 0>, <CRCT1, causes(num_study), Asthma, 10>, and <CRCT1, causes(in_population_type), Asthma, 3>. For example, the information input of <CRCT1, causes(num_study), Asthma, 10> may represent that ten (10) research studies teach that the CRCT1 gene causes the asthma disease.

In one implementation, a loss value for each of these models may be determined. For example, the importance model may output a significance loss value 718 (denoted as Lossimp) based on the important inputs. The information model may output a predicate metadata loss value 728 (denoted as Lossinfo) based on the information inputs. An overall loss value 738 may be determined based on the significance loss value 718 and the predicate metadata loss value 728 according to a loss function 730. For example in one implementation, the loss function 730 may be defined as $L = \alpha_1 \text{Lossinfo} + \alpha_2 \text{Lossimp}$, where $\alpha_1$ and $\alpha_2$ are trainable weights.

In an embodiment, the method 100 in FIG. 1 may include determining model parameters, i.e. trainable weights. In some implementations, a loss function may be minimized in order to learn optimal parameters that best discriminate positive statements from negative statements. Exemplary optimizers may also be utilized, including the following optimization algorithms: stochastic gradient descent (SGD), adaptive moment estimation (Adam), and the gradient-based optimization algorithm (Adagrad).

The method 100 may include determining a trained model based on the minimized overall loss value. In certain embodiments, the overall loss value may be minimized via a machine learning model. The method 100 may utilize an optimizer 740 in FIG. 7 to obtain optimized model parameters 745 and determine a probability of existence (or a likelihood score) 750 of a link between a gene and a disease based on the trained model. For example but not limited to, the probability of existence 750 may include a knowledge graph embeddings (KGE) score. The KGE scoring algorithm may include one or more of TransE, RESCAL, DistMult, ComplEx, and/or ConvE.

In one implementation, referring to 760 in FIG. 7, the method may further include determining whether the probability of existence is larger than a preset threshold. In response to the determination that the probability of existence is larger than the preset threshold, the method may further include updating the knowledge graph with the link (referring to 770 in FIG. 7). In another implementation, in response to the determination that the probability of existence is not larger than the preset threshold, the method may further include marking the present link with a warning message or removing the present link (referring to 780 in FIG. 7). The warning message may include the probability of existence corresponding to the link.

Figure 8:
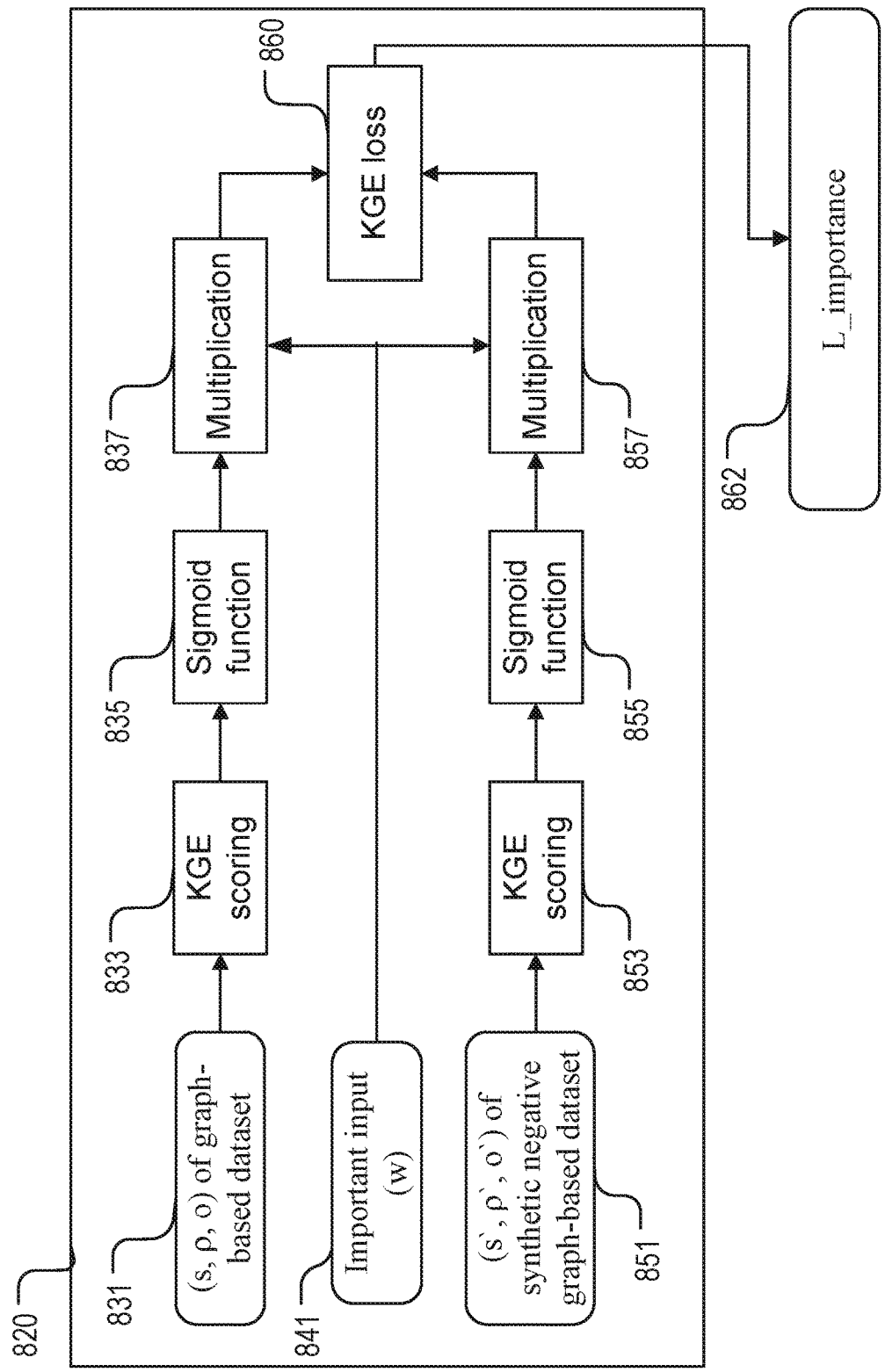
FIG. 8 is a schematic diagram of an importance model, in accordance with certain embodiments of the present disclosure.

Referring to FIG. 8, an embodiment of an importance model 820 is described. The important model 820 may be an exemplary implementation of the important model 715 in FIG. 7.

Important inputs may include a portion or all of s, p, o, and w, where s is a subject of the resource or knowledge base, o is an object, p is a predicate that denotes traits or aspects of the resource that express the relationship or link between the subject and the object in a graph-based dataset format, and w is the significance parameter. In one implementation, the significance parameter w may be normalized and scaled to the range between 0 and 1, inclusive (i.e., [0, 1]).

The s, p, and o of the graph-based dataset 831 may be utilized as input to a scoring model 833 to generate a positive structural score. For example but not limited to, the scoring model 833 may include a KGE scoring model. The generated positive structure sore may be utilized as input to a non-linear function 835, for example, a sigmoid function to generate a normalized positive structure score. The normalized positive structure score may be utilized as input to a multiplication function 837. The multiplication function 837 may also take the significance parameter w 841 of the important input as input to generate an adjusted positive structural score. In one implementation, for example, the adjusted positive structural score may be calculated as (1−w) multiplied by the normalized positive structure score.

The s', p', and o' of the synthetic negative graph-based dataset 851 may be utilized as input to a scoring model 853 to generate a negative structural score. For example but not limited to, the scoring model 853 may include a KGE scoring model. In one implementation, the synthetic negative graph-based dataset may not be a part of the input from the knowledge graph, and may be generated by a generator for synthetic negative graph-based datasets. The generated negative structure sore may be utilized as input to a non-linear function 855, for example, a sigmoid function to generate a normalized negative structure score. The normalized negative structure score may be utilized as input to a multiplication function 857. The multiplication function 857 may also take the significance parameter w 841 of the important input as input to generate an adjusted negative structural score. In one implementation, for example, the adjusted negative structural score may be calculated as an actual significance parameter ($w_{act}$) multiplied by the normalized negative structure score, where the actual significance parameter ($w_{act}$) may be selected from one of the following: $w_{struc}+(1-w_{struc})*w$; or a larger value between $w_{struc}$ and w, where $w_{struc}$ is a structural significance parameter and may be used to preserve structural constraints when w is within a range between 0 and 1.

A loss calculation function 860 may generate a significance loss value 862 ($Loss_{imp}$) based on the adjusted positive structural score and the adjusted negative structural score. For example but not limited to, the loss calculation function 860 may include a KGE loss function. The KGE loss function 860 may generate and output a importance loss value 862 (L_importance). In one implementation, the importance loss value may be a significance loss value ($Loss_{imp}$), which is a partial sub-loss for importance that contributes to a global loss.

Figure 9:
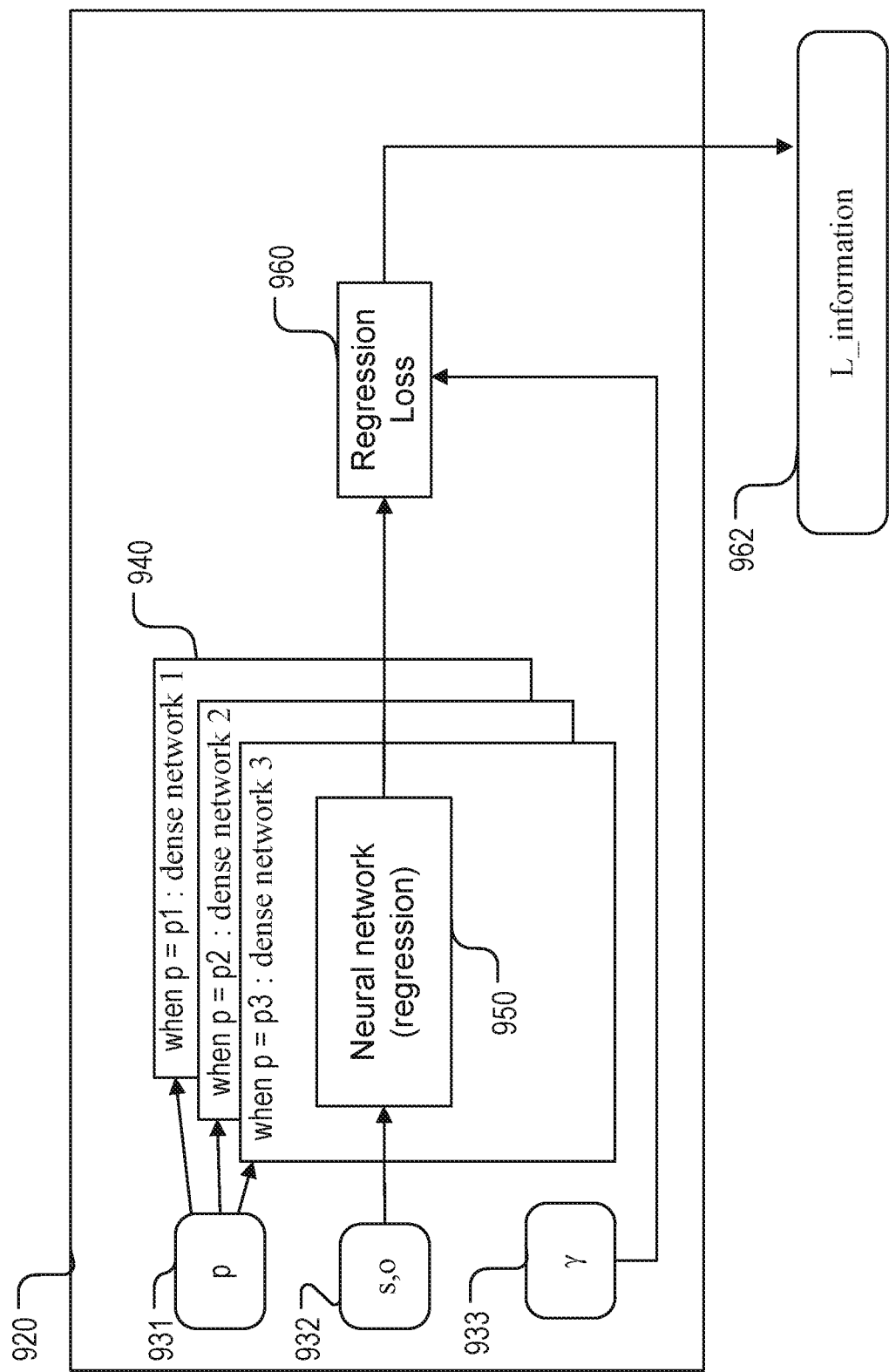
FIG. 9 is a schematic diagram of an information model, in accordance with certain embodiments of the present disclosure.

Referring to FIG. 9, an embodiment of an information model 920 is described. The information model 920 may be an exemplary implementation of the information model 725 in FIG. 7.

Information inputs may include a portion or all of s, p, o, and r, where s is the subject of the resource or knowledge base, o is the object, p is the predicate that denotes traits or aspects of the resource that express the relationship or link between the subject and the object in a graph-based dataset format, and γ is numerical attributes and may include [$\gamma_1, \ldots, \gamma_n$] informational-type numerical attributes. In one implementation, the numerical attribute S may be normalized by subtracting the mean and dividing it by the standard deviation.

In some implementations, the predicate p may be utilized to select or determine a correct dense network among a group of dense networks 940. In one implementation, for each predicate type, there may be one corresponding dense network. The group of dense networks 940 in FIG. 9 includes three dense networks. For other implementations, the group of dense networks may include fewer or more than three dense networks.

Each dense network may comprise a neural network 950. In one implementation, for a neural network, the number of links of each node may be close to the maximum number of nodes. Each node may be linked to almost all other nodes in the knowledge graph.

The neural network 950 may generate a predicate numerical attribute ($\gamma_{pred}$). A regression loss function 960 may utilize the predicate numerical attribute ($r_{pred}$) and the numerical attributes 933 (r) as input to generate an information loss value 962 (L_information). In one implementation, the information loss value may be a predicate metadata loss value ($Loss_{info}$). The information loss value may be a partial sub-loss contributing to the global loss. In another implementation, the partial sub-loss may be for an additional information vector. In another implementation, the regression loss function 960 may determine a normalized numerical attribute and determine a regression loss such as a root mean square error (RMSE) based on the normalized numerical attribute. The output of the information model may include the regression loss including the predicate metadata loss value ($Loss_{info}$).

The disclosed graph-based dataset format and schemas may provide the advantage of intelligently integrating the knowledge base into structured models and datasets to enable deep learning processes and systems that provide an improved analysis of genes associated with certain diseases. The RDF format differs from relational database tables, whose relations are pre-defined at design time and are implicit across the rows and columns of a table. Instead, RDF relationships may be stored as properties. In a graph-based representation, these properties may be associated with the edges that connect vertices in the knowledge graph. This storage of the relationships provides the context for interpretation of the parameters or attributes for the genes and diseases. Further, storage of the relationship in addition to the parameter allows for alteration of the relationship without altering the parameter, and vice versa. The independent adjustment of these factors allows the logic to support extensions or changes to the knowledge base via an adjustment of parameters or relationships, rather than using a single degree of freedom. In an embodiment, these storage formats and datasets may benefit the identification and analysis of genes for diseases.

In certain embodiments, the enhanced level of structured data offered by knowledge graphs may be utilized to identify new genes-disease associations extracted from the existing information received from a knowledge base. However, the features described herein are applicable to knowledge graphs of data representing various fields of biology, genetics and medicine. Data may be extracted from various data sources into a knowledge graph.

In some embodiments, the data sources may include metadata sources and raw data sources. Metadata sources may include datasets that may assist with mapping the raw data sources. In addition, the metadata sources may provide information to facilitate annotation. In certain embodiments, the metadata source may be designed to allow other reference ontologies and schemas to be mapped to it, and may enable the determination of broader relationships. For example, the ChEMBL, Ensembl and Experimental Factor Ontology (EFO) datasets may be utilized in the data mapping process, in accordance with certain embodiments. Raw data sources may be utilized within the training process. In some embodiments, the following data-sources may be implemented: GWAS, StringDB, GeneAtlas, GTEX, NealeLab, and/or PheWeb. The data mapping process may include the generation of a catalogue where the phenotype ontologies found across various data sources are mapped to one Standard Disease Ontology (SDO). Accordingly, this may maintain key mappings between the various data sources that are used for merging the raw datasets together. The data mapping process may utilize the metadata, as described above.

In addition to the aforementioned data sources, a system may include a data engineering layer, a graph schema, an unified visualization, an analytics pipeline, a weights generation pipeline, analytics models, an inference pipeline, and a result storage.

Figure 10:
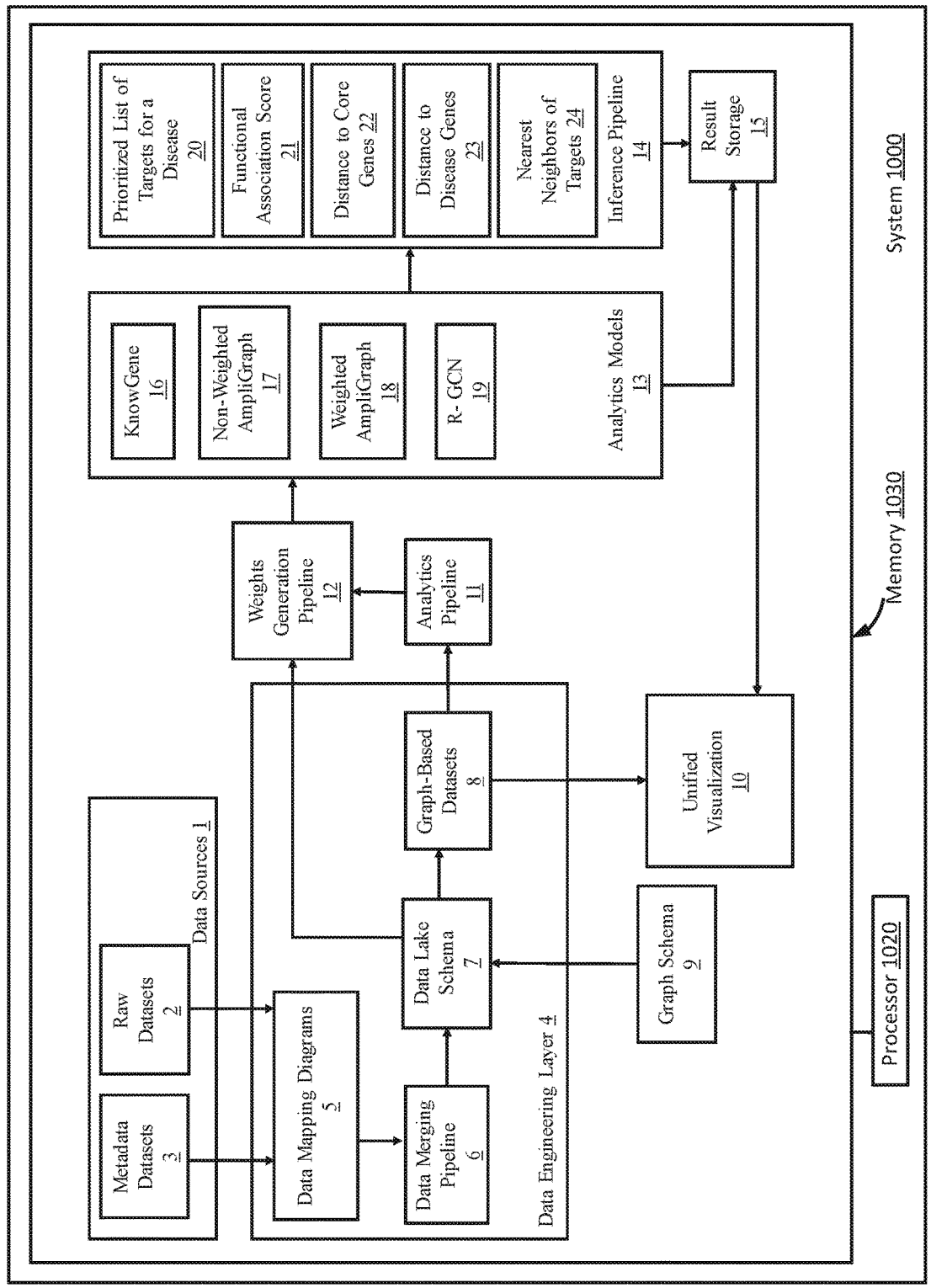
FIG. 10 is a block diagram illustrating an example of an architecture for an exemplary system, in accordance with certain embodiments of the present disclosure.

FIG. 10 illustrates an embodiment of a system 1000 that may be implemented in many different ways, using various components and modules, including any combination of circuitry described herein, such as hardware, software, middleware, application program interfaces (APIs), and/or other components for implementing the features of the circuitry such as a processor 1020 and memory 1030. The system 1000 may include, for example: data sources 1 including raw datasets 2 and metadata datasets 3; a data engineering layer 4 including data mapping diagrams 5, a data merging pipeline 6, a data lake schema 7, and graph-based datasets 8; a graph schema 9; an unified visualization 10; an analytics pipeline 11; a weights generation pipeline 12; analytics models 13; an inference pipeline 14; and a result storage 15. The analytics models 13 may include may include: a knowledge-based model for predicting gene-disease associations, such as the KnowGene model 16; a non-weighed model, such as the Non-Weighted AmpliGraph model 17; a weighted model, such as the Weighted AmpliGraph model 18; and a Relational Data with Graph Convolutional Networks (R-GCN) model 19. The inference pipeline 14 may include: a prioritized list 20 of targeted genes for a disease, a functional association score 21, a first distance 22 between a targeted gene and core genes, a second distance 23 between a targeted gene and disease genes, and nearest neighbors 24 of targeted genes.

In some embodiments, the data sources 1 may include numerous raw data sources and numerous metadata sources. Metadata datasets 3 may be extracted from the metadata sources, and raw datasets 2 may extracted from the raw data sources. The metadata datasets 3 may be configured to map the raw datasets 2 received from the raw data sources. For example, one raw dataset 2 may reference the disease commonly known as diabetes, while another raw dataset 2 may refer to the same disease by using its formal name, diabetes mellitus. The extracted metadata datasets 3 may associate key identifiers from the two raw datasets 2. In addition, the extracted metadata datasets 3 may provide information to facilitate annotation of the extracted raw datasets 2. As an application ontology, the metadata datasets 3 may be configured to allow other reference ontologies to be mapped to it, and may enable the determination of broader relationships. For example, the ChEMBL, Ensembl and EFO metadata sources may be utilized in the data mapping process, in accordance with embodiments of the present disclosure. The ChEMBL is a data source 1 that may provide information about known drugs. The Ensembl or EQTL data source 1 may provide information relating to associations between gene identifier and gene labels. EFO metadata datasets 3 may include information relating to disease anthologies, which may be used for annotations and/or mapping datasets received from raw data sources 2. Raw data sources may be utilized within the training process. In certain embodiments, the following raw data sources may be implemented: genome-wide association study (GWAS), SpringDB, GeneAtlas, Genotype-Tissue Expression (GTEX), NealeLab, and/or PheWeb.

The data engineering layer may include a data-mapping knowledge base, a data merging pipeline, a data lake schema, and the generation of graph-based datasets. The data merging pipeline may comprise an end-to-end pipeline that includes the downloading of data-sources, the merging of data-sources (based on the data mapping pipeline), and the storing of such data-sources in a data lake. The data merging pipeline may consists of downloading the agreed datasets, which may be received in different formats. The datasets may be processed to clean the data, and reformat the data into a format that may be merged together using the key mappings from the catalogue. After the data is mapped, it may be stored in a unified format on the data lake where it can be queried for further processes.

The data lake schema may include a repository of data stored in a natural/raw format. In some embodiments, the data lake may contain the merged datasets discussed above. The data sources may be combined together in an unified format, which may be mapped using keys and stored on data lake. This data may be the source of the analytics pipeline, and may be used for visualisation and analysis in the analytics pipeline.

The step of generating graph-based dataset may include defining the columns requested from each data source. The data in such columns may become the subjects and objects for the graph-based datasets, and the predicates that tie the two entities together are defined. In certain embodiments, this step must be conducted for every new dataset. This step may result in the graph-based dataset that are used in the analytics models.

The graph schema may include a blueprint for generating the knowledge graph. This may include definitions for the entities, concepts and data that may be used in the analytics models. The data-lake schema may be based on this defined graph schema. In certain embodiments, a knowledge graph schema may include information pertaining to genes and diseases that are known to be associated with them. Each node of the knowledge graph may include information, and each edge may represent a relationship between the information included in the nodes.

In an embodiment, the unified visualization may include a graphical user interfaces (GUIs). The visualization step may include, or represent, the rationale showing why a certain gene may be ranked highly. Visualisations may be generated on the distance to 'core genes', the 'nearest neighbours' in the embeddings space, and the connected entities in the graph. The inference pipeline for link prediction may include, or represent: a prioritized list of genes associated with a disease, a functional association score, a distance to core-genes, a distance to disease genes, and the nearest neighbors of the genes. In an embodiment, the weights generation pipeline may generate the weights utilized for the analytics models. In some embodiments, the weights may include: disease-to-variant; and, gene-to-variant. Both such weights may be derived from GWAS and GTEX data.

In certain embodiments, the KnowGene may include a machine learning model to target identification. It may utilize PPI (gene-gene data from HIPPIE) and gene-disease relation data from GWAS and OMIM in order to predict genes that are associated with a given disease. The KnowGene approach may provide a benchmark for the novel analytics approaches presently herein. Knowledge graphs may represent graph-based knowledge bases having facts modelled as relationships between entities.

Upon generation of a knowledge graph, a neural architecture may be built to generate embeddings of complex entities, in accordance with certain embodiments. From these embeddings, scoring functions may perform tasks, such as link prediction. In some embodiments, this logic may be implemented to discover new relations between diseases and genes. A non-weighted model or a weighted model may be implemented. Additional information about the links between entities in the graph may be used during training. This information may be incorporated in order to update the embeddings of each entity to improve the accuracy of the predictions. In an embodiment, the R-GCN model may be utilized as a machine learning approach for building ontologies based on a graph structure. The R-GCN model may be used to represent genetic information in a graph, and to discover new relations between diseases and genes.

In some embodiments, a model may utilize a test set of verified, validated gene targets so that the models' performance can be evaluated. This may include a prioritized list of gene targets for a disease. In an example concerning a set of validated targets for rheumatoid arthritis, the analytics models may be assigned with the task of predicting genes for rheumatoid arthritis. The validated dataset may be used with a binary classification, and/or learn-to-rank metrics, for measuring the performance of a model.

The Functional Association Score may be utilized by the KnowGene machine learning model. For example, this metric may consider the co-occurrences of a query gene with known disease genes. In an embodiment, it may compare the joint probability of the query gene and the disease gene occurring together in a disease against the probability of them occurring independently in a disease. The functional association score may be defined as follows:

$$S(D,g_x) = \Sigma_{g_y \in D} P(g_x, g_y) I(g_x, g_y),$$

where $$I(g_x, g_y) = \log \frac{P(g_x, g_y)}{P(g_x)P(g_y)},$$

and where $P(g_x)$, $P(g_y)$ are the probabilities of observing genes $g_x$ and $g_y$, independently in a given disease, and $P(g_x,g_y)$ is the probability of observing genes $g_x$ and $g_y$, together in a given disease D. Distance-to-core genes may also be utilized by the KnowGene model. Core genes may include the genes in the largest statistically significant connected cluster in the interactome (gene-gene interaction network). Statistical testing may be conducted to ensure that the largest connected cluster is not just randomly formed.

In addition, the distance-to-disease genes may also be utilized by the KnowGene model. A unit network distance may be defined as a path from one protein to another with a direct connection in the interactome. The shortest distances of a query gene to all the known genes of a given disease from 1 to 10 may be identified. Such distances may be binned. Each bin may be filed with the number of genes known to be associated with the given disease. For example, given a vector $(n_1, n_2, \ldots, n_{10})$ with $\Sigma n_i = N_g$, $N_g$ may be the total number of known genes and $n_i$ may be the number of genes in the known set with shortest distance i to the unknown gene.

For a given target, in an embodiment, the nearest neighbours may be identified by calculating the cosine similarity of the target's embedding against all other embeddings in the dataset. This method may add another layer that provides an explanation of the association between a target and a disease, and may allow users to explore the embedding space. The result storage may include a platform that may be utilized to store the results and trained models created within the analytics pipeline.

Figure 11:
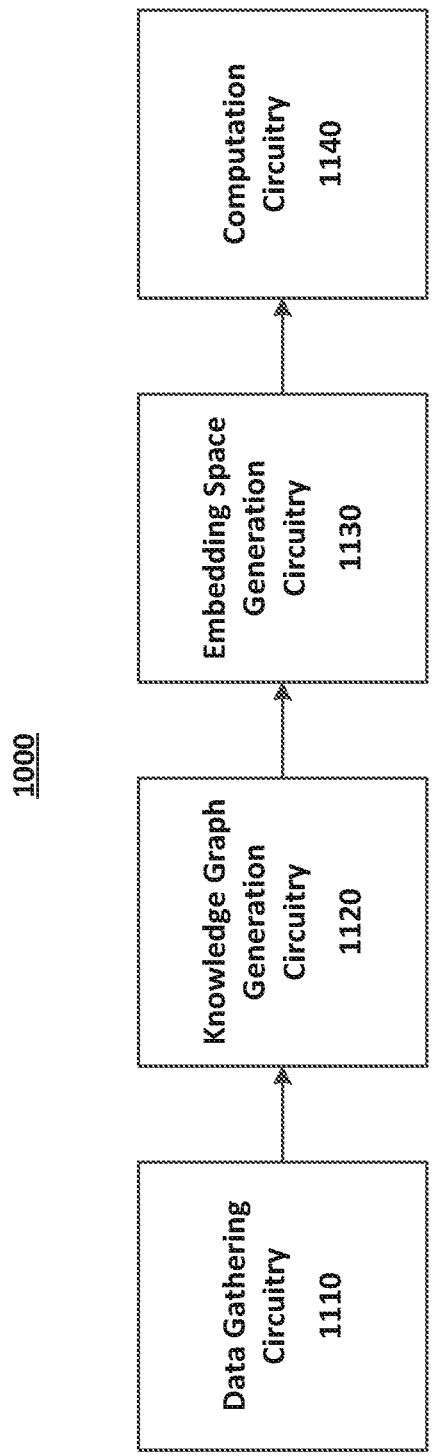
FIG. 11 is a block diagram illustrating an embodiment of a system, in accordance with certain embodiments of the present disclosure.

Referring to FIG. 11, in some embodiments, a data gathering circuitry 1110 may be configured to receive human data, such as genetic information and disease information. A knowledge graph generation circuitry 1120 may be configured to generate a graphically represented data structure model based on the received dataset. The knowledge graph generation circuitry 1120 may construct a knowledge graph from the received information that is mapped to a predefined graph schema, in accordance with certain embodiments. The resulting graphical representation may provide a specific format of structured data where each connecting edge represents a relationship between nodes. The knowledge graph generation circuitry 1120 may further train the knowledge graph, in accordance with certain embodiments.

The system 1000 may further include an embedding space generation circuitry 1130 that may be configured to generate embedding spaces based on knowledge graphs. The embedding space generation circuitry 1130 may convert the data and relationships represented in the knowledge graph into a plot of nodes within an embedding space. The generated embedding space may include vector nodes (e.g., vector set of triplets) representing the structured information included in the knowledge graph.

In some embodiments, the system 1000 may include a computation circuitry 1140 for implementing computations within the embedding space. For example, the computation circuitry 1140 may be configured to: determine a plurality of candidate statements; determine a weighting from the combination index (CI) database based on the query; determine a score for each candidate statement based on the query and based on the weighting using the embedding space for the knowledge graph; analytics modeling; and/or, rank the predicted links between the target and a disease. The computation circuitry 1140 may enable the modeling of weighting in order to score the prediction of the relationship between a target and a disease. In addition, the computation circuitry 1140 may identify gap regions within the region of interest, and compute Max-Min Multi-dimensional computations to determine a center for the gap regions within the region of interest. The computation circuitry 1140 is further configured to consider that center node to be an embedding of a newly discovered gene target that was not present in the original knowledge graph. This may be technically implemented by generating a new node within the embedding space at the determined center having the attributes of the newly discovered target. Overall, executing the scoring process provides improvements to the computing capabilities of a computer device executing the process by reducing the search space and by allowing for more efficient data analysis to analyze large amounts of data in a shorter amount of time.

In an embodiment, a system for predicting node-to-node links may include a memory to store executable instructions and a processor adapted to access the memory. The processor may be adapted to execute the executable instructions stored in the memory to perform certain steps. In some embodiments, the initial step may include receiving a knowledge graph based on a knowledge base. The knowledge graph may represent links or predicates between a gene and a disease. The knowledge base may include data that identifies an association of the gene with the disease. The data may be stored in a graph-based dataset format in memory. In certain embodiments, the initial step may include receiving a knowledge base, and generating a knowledge graph based on the knowledge base.

In an embodiment, the system may include the step of assigning a set of predicate metadata parameters to each graph-based dataset of the knowledge base. The number of predicate metadata parameters in each set may depend on the predicate type for the corresponding graph-based dataset. In certain embodiments, the system may include the step of assigning a significance parameter to each triple dataset of the knowledge base. In some embodiments, the received knowledge base and/or the received knowledge graph may include assigned predicate metadata parameters that are assigned to each triple dataset, and assigned significance parameter that are assigned to each triple dataset.

In an embodiment, the system may include the steps of determining a positive structural score for each graph-based dataset of the knowledge base, and adjusting the positive structural score based on the significance parameter. The neural networks, or machine-learning models, may be trained on both true and false concepts, which may be represented by the positive and synthetic negative graph-based datasets respectively. In certain embodiments, the system may include the steps of generating a set of synthetic negative graph-based datasets, determining a negative structural score for each graph-based dataset of the set of synthetic negative graph-based dataset, and adjusting the negative structural score based on the significance parameter. In some embodiments, the system may include the steps of determining a significance loss value based on the adjusted positive structural score and the adjusted negative structural score. In some embodiments, the system may further include the steps of determining a likelihood score of a link between a third node and a fourth node in the knowledge graph based on the significance loss value.

In an embodiment, the processor may further be adapted to generate a set of predicate metadata parameters based on a plurality of neural networks. The generated set of predicate metadata parameters may include the set of predicate metadata parameters assigned to each graph-based dataset of the knowledge base. The processor may also be adapted to determine a predicate metadata loss value for the assigned set of predicate metadata parameters.

In certain embodiments, the processor may be adapted to determine an overall loss value based on the significance loss value and the predicate metadata loss value, and minimize the overall loss value based on a machine learning model. The processor may also be adapted to determine a trained model based on the minimized overall loss value, receive a real-time user input request of a graph-based dataset, and determine a likelihood score of a link between the at least one gene and the at least one disease based on the trained model and the user input request.

While the present disclosure has been particularly shown and described with reference to an embodiment thereof, it will be understood by those skilled in the art that various changes in form and details may be made therein without departing from the spirit and scope of the present disclosure. Although some of the drawings illustrate a number of operations in a particular order, operations that are not order-dependent may be reordered and other operations may be combined or broken out. While some reordering or other groupings are specifically mentioned, others will be apparent to those of ordinary skill in the art and so do not present an exhaustive list of alternatives.

What is claimed is:

1. A system for predicting node-to-node links in a knowledge graph, comprising:
   a memory to store executable instructions; and
   a processor adapted to access the memory, the processor further adapted to execute the executable instructions stored in the memory to:
      receive a knowledge graph based on a knowledge base, the knowledge graph comprising a link between a first node and a second node, the first and second nodes representing associated objects, the knowledge base comprising a graph-based dataset stored in the memory, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph,
      determine a positive structural score for each triple in the knowledge graph,
      adjust each positive structural score based on each corresponding significance parameter,
      generate a synthetic negative graph-based dataset based on the graph-based dataset, the synthetic negative graph-based dataset comprising a set of synthetic negative triples,
      determine a negative structural score for each synthetic negative triple of the synthetic negative graph-based dataset,
      adjust each negative structural score based on each corresponding significance parameter,
      determine a significance loss value based on the adjusted positive structural scores and the adjusted negative structural scores, and
      determine a likelihood score of a link between a third node and a fourth node in the knowledge graph based on the significance loss value by:
         determining a predicate metadata loss value for the set of predicate metadata,
         determining an overall loss value based on the significance loss value and the predicate metadata loss value;
         minimizing the overall loss value based on a machine learning model;

determining a trained model based on the minimized overall loss value;

receiving a real-time user input request of a graph-based dataset; and determining the likelihood score of the link between the third node and the fourth node based on the trained model and the user input request.

2. The system of claim 1, wherein the processor is further adapted to:

generate a set of predicate metadata parameters based on a plurality of neural networks by means of a regression loss, wherein the generated set of predicate metadata parameters comprise the set of predicate metadata parameters assigned to each graph-based dataset of the knowledge base.

3. The system of claim 1, wherein the processor is further adapted to:

determine whether the likelihood score of the link is larger than a preset threshold; and in response to the determination that the likelihood score is larger than the preset threshold, update the knowledge graph with the link.

4. The system of claim 3, wherein the processor is further adapted to:

in response to the determination that the likelihood score is not larger than the preset threshold, mark the link with a warning message.

5. A method for predicting node-to-node links in a knowledge graph, comprising:

receiving, by a device comprising a memory storing instructions and a processor in communication with the memory, a knowledge graph based on a knowledge base, the knowledge graph comprising a link between a first node and a second node, the first and second nodes representing associated objects, the knowledge base comprising a graph-based dataset stored in the memory, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph, determining, by the device, a positive structural score for each triple in the knowledge graph, adjusting, by the device, each positive structural score based on each corresponding significance parameter, generating, by the device, a synthetic negative graph-based dataset based on the graph-based dataset, the synthetic negative graph-based dataset comprising a set of synthetic negative triples, determining, by the device, a negative structural score for each synthetic negative triple of the synthetic negative graph-based dataset, adjusting, by the device, each negative structural score based on each corresponding significance parameter, determining, by the device, a significance loss value based on the adjusted positive structural scores and the adjusted negative structural scores, and determining, by the device, a likelihood score of a link between a third node and a fourth node in the knowledge graph based on the significance loss value by:

determining a predicate metadata loss value for the set of predicate metadata, determining an overall loss value based on the significance loss value and the predicate metadata loss value;

minimizing the overall loss value based on a machine learning model;

determining a trained model based on the minimized overall loss value;

receiving a real-time user input request of a graph-based dataset; and determining the likelihood score of the link between the third node and the fourth node based on the trained model and the user input request.

6. The method of claim 5, further comprising:

generating, by the device, a set of predicate metadata parameters based on a plurality of neural networks by means of a regression loss, wherein the generated set of predicate metadata parameters comprise the set of predicate metadata parameters assigned to each graph-based dataset of the knowledge base.

7. The method of claim 5, further comprising:

determining, by the device, whether the likelihood score of the link is larger than a preset threshold; and in response to the determination that the likelihood score is larger than the preset threshold, updating, by the device, the knowledge graph with the link.

8. The method of claim 7, further comprising:

in response to the determination that the likelihood score is not larger than the preset threshold, marking, by the device, the link with a warning message.

9. A product comprising:

machine-readable media other than a transitory signal;

instructions stored on the machine-readable media for optimizing hyper-parameters for a machine-learning model under constraints; and wherein when a processor executes the instructions, the product is configured to:

receive a knowledge graph based on a knowledge base, the knowledge graph comprising a link between a first node and a second node, the first and second nodes representing associated objects, the knowledge base comprising a graph-based dataset stored in the machine-readable media, the graph-based dataset associating the first node with the second node, the graph-based dataset of the knowledge base comprising a set of predicate metadata assigned to each triple in the knowledge graph, the graph-based dataset of the knowledge base comprising a significance parameter assigned to each triple in the knowledge graph, determine a positive structural score for each triple in the knowledge graph, adjust each positive structural score based on each corresponding significance parameter, generate a synthetic negative graph-based dataset based on the graph-based dataset, the synthetic negative graph-based dataset comprising a set of synthetic negative triples, determine a negative structural score for each synthetic negative triple of the synthetic negative graph-based dataset, adjust each negative structural score based on each corresponding significance parameter, determine a significance loss value based on the adjusted positive structural scores and the adjusted negative structural scores, and determine a likelihood score of a link between a third node and a fourth node in the knowledge graph based on the significance loss value by:

determining a predicate metadata loss value for the set of predicate metadata, determining an overall loss value based on the significance loss value and the predicate metadata loss value;

minimizing the overall loss value based on a machine learning model;

determining a trained model based on the minimized overall loss value;

receiving a real-time user input request of a graph-based dataset; and determining the likelihood score of the link between the third node and the fourth node based on the trained model and the user input request.

10. The product of claim 9, wherein, when the processor executes the instructions, the product is further configured to:

generate a set of predicate metadata parameters based on a plurality of neural networks by means of a regression loss, wherein the generated set of predicate metadata parameters comprise the set of predicate metadata parameters assigned to each graph-based dataset of the knowledge base.

11. The product of claim 9, wherein, when the processor executes the instructions, the product is further configured to:

determine whether the likelihood score of the link is larger than a preset threshold;

in response to the determination that the likelihood score is larger than the preset threshold, update the knowledge graph with the link; and in response to the determination that the likelihood score is not larger than the preset threshold, mark the link with a warning message.

* * * * *

UNITED STATES PATENT AND TRADEMARK OFFICE
CERTIFICATE OF CORRECTION

PATENT NO. : 11,593,665 B2
APPLICATION NO. : 16/892916
DATED : February 28, 2023
INVENTOR(S) : Sumit Pai et al.

It is certified that error appears in the above-identified patent and that said Letters Patent is hereby corrected as shown below:

In the Specification

Column 13, Line 34, delete "s', p', and o'" and insert in its place -- s`, ρ`, and o` --.

Column 14, Line 12, delete "S" and insert in its place -- δ --.

Signed and Sealed this
Twenty-third Day of May, 2023

Katherine Kelly Vidal
*Director of the United States Patent and Trademark Office*